(12) United States Patent
Ilan et al.

(10) Patent No.: US 10,137,221 B2
(45) Date of Patent: *Nov. 27, 2018

(54) HEMOSTATIC MIXTURE OF CELLULOSE-BASED SHORT AND LONG FIBERS

(71) Applicants: Omrix Biopharmaceuticals Ltd., Rehovot (IL); Ethicon, Inc., Somerville, NJ (US)

(72) Inventors: Erez Ilan, Kibbutz Netzer Sereni (IL); Omri Faingold, Ness Ziona (IL); Nataly Freizus, Arad (IL); Ronen Eavri, Binyamina (IL); Dwayne Looney, Flemington, NJ (US); Sridevi Dhanaraj, Raritan, NJ (US); James Galloway, Bridgewater, NJ (US); Walter Danker, Newtown, PA (US)

(73) Assignees: Omrix Biopharmaceuticals Ltd., Rehovot (IL); Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/346,236

(22) Filed: Nov. 8, 2016

(65) Prior Publication Data
US 2017/0128616 A1 May 11, 2017

Related U.S. Application Data

(60) Provisional application No. 62/252,785, filed on Nov. 9, 2015, provisional application No. 62/252,796, filed on Nov. 9, 2015.

(30) Foreign Application Priority Data

Nov. 8, 2015 (IL) .......................... 242496
Nov. 8, 2015 (IL) .......................... 242497

(51) Int. Cl.
| | | |
|---|---|---|
| A61L 24/08 | (2006.01) |
| A61L 24/02 | (2006.01) |
| A61L 24/00 | (2006.01) |
| A61L 26/00 | (2006.01) |
| A61L 24/04 | (2006.01) |
| A61L 24/06 | (2006.01) |

(52) U.S. Cl.
CPC ......... *A61L 26/0023* (2013.01); *A61L 24/001* (2013.01); *A61L 24/0015* (2013.01); *A61L 24/02* (2013.01); *A61L 24/043* (2013.01); *A61L 24/06* (2013.01); *A61L 24/08* (2013.01); *A61L 26/00* (2013.01); *A61L 26/0004* (2013.01); *A61L 2300/106* (2013.01); *A61L 2300/232* (2013.01); *A61L 2300/25* (2013.01); *A61L 2300/418* (2013.01); *A61L 2300/802* (2013.01); *A61L 2400/04* (2013.01)

(58) Field of Classification Search
CPC .. A61L 26/0023; A61L 26/00; A61L 26/0004; A61L 2300/106; A61L 2300/25; A61L 2300/418; A61L 2400/04; A61L 24/08; A61L 24/02; A61L 24/00
See application file for complete search history.

(56) References Cited

U.S. PATENT DOCUMENTS

| | | |
|---|---|---|
| 1,540,979 A | 6/1925 | Bloom |
| 3,364,200 A | 1/1968 | Ashton et al. |
| 4,626,253 A | 12/1986 | Broadnax, Jr. |
| 4,637,815 A | 1/1987 | Lemole |
| 4,749,689 A | 6/1988 | Miyata et al. |
| 5,180,398 A | 1/1993 | Boardman et al. |
| 5,403,278 A | 4/1995 | Ernst et al. |
| 5,484,913 A | 1/1996 | Stillwell et al. |
| 5,643,596 A | 7/1997 | Pruss et al. |
| 5,645,849 A | 7/1997 | Pruss et al. |
| 5,696,191 A | 12/1997 | Nohr et al. |
| 6,056,970 A * | 5/2000 | Greenawalt ............ A61L 15/32 424/422 |
| 6,225,461 B1 | 5/2001 | Akimoto et al. |
| 6,309,454 B1 | 10/2001 | Harvey et al. |
| 6,627,749 B1 | 9/2003 | Kumar |
| 7,923,031 B2 | 4/2011 | Moller |
| 8,722,081 B2 | 5/2014 | Filatov et al. |
| 8,815,832 B2 | 8/2014 | Wang et al. |
| 9,131,929 B2 | 9/2015 | MacPhee et al. |
| 2002/0192271 A1 | 12/2002 | Hedner et al. |
| 2004/0005350 A1 | 1/2004 | Looney et al. |
| 2006/0233869 A1 | 10/2006 | Looney et al. |
| 2008/0027365 A1 | 1/2008 | Huey |
| 2008/0138387 A1 | 6/2008 | Machiraju |
| 2009/0062233 A1 | 3/2009 | Ji et al. |
| 2012/0253298 A1 | 10/2012 | Henderson et al. |

(Continued)

FOREIGN PATENT DOCUMENTS

| | | |
|---|---|---|
| AU | 2013218367 B2 | 8/2013 |
| CA | 2688196 C | 1/2009 |

(Continued)

OTHER PUBLICATIONS

English Translation of EP 0 216 378 A2 (published Sep. 1986).*
Cullen, B. et al 'The role of oxidized regenerated cellulose/collagen in chronic wound repair and its potential mechanism of action' The International Journal of Biochemistry & Cell Biology 34 (2002) pp. 1544-1556.
Howsmon et al 'The Ball-Milling of Cellulose Fibers and Recrystallization Effects' Journal of Applied Polymer Science (1959) vol. 1 Issue 3 pp. 313-322.
Rajkhowa, R., Wang, L., & Wang, X. (2008). Ultra-fine silk powder preparation through rotary and ball milling. Powder Technology, 185(1), 87-95. doi:10.1016/j.powtec.2008.01.005.

(Continued)

*Primary Examiner* — Blessing M Fubara
(74) *Attorney, Agent, or Firm* — David R. Crichton

(57) ABSTRACT

The invention relates to a hemostatic composition comprising a mixture of cellulose-based short and long fibers, preparation and use thereof.

6 Claims, 1 Drawing Sheet

(56) References Cited

U.S. PATENT DOCUMENTS

| | | | |
|---|---|---|---|
| 2013/0310873 A1 | 11/2013 | Stopek et al. | |
| 2013/0316974 A1* | 11/2013 | Wang | A61L 26/009 514/57 |
| 2013/0345678 A1* | 12/2013 | Rubin | A61F 13/148 604/515 |
| 2015/0017225 A1 | 1/2015 | Hubbell et al. | |
| 2016/0074602 A1* | 3/2016 | Wang | A61M 11/007 604/518 |

FOREIGN PATENT DOCUMENTS

| | | |
|---|---|---|
| CN | 1850111 A | 10/2006 |
| CN | 104013991 A | 9/2014 |
| EP | 0 216 378 A2 * | 9/1986 |
| EP | 1323436 | 7/2003 |
| EP | 2203053 A1 | 7/2009 |
| EP | 1731175 B1 | 9/2009 |
| EP | 2233157 A1 | 9/2010 |
| EP | 1641399 B1 | 9/2012 |
| PH | 32014 A | 6/1999 |
| RU | 2235539 C1 | 9/2004 |
| RU | 2522879 | 7/2014 |
| WO | WO 1990013320 A1 | 11/1990 |
| WO | WO 1996/040033 A1 | 12/1996 |
| WO | WO 2001/024841 A1 | 4/2001 |
| WO | WO 2002/024239 A1 | 3/2002 |
| WO | WO 2007/076415 | 7/2007 |
| WO | WO 2009/091549 | 7/2009 |

OTHER PUBLICATIONS

Sergeant, P., Kocharian, R., Patel, B., Pfefferkorn, M., & Matonick, J. (2016). Needle-to-suture ratio, as well as suture material, impacts needle-hole bleeding in vascular anastomoses. Interactive CardioVascular and Thoracic Surgery, 22(6), 813-816. doi:10.1093/icvts/ivw042.

Yasnitskii et al., 'Oxycelodex, a new hemostatic preparation' Pharmaceutical Chemistry Journal, 18 pp. 506-5.

International Search Report re: PCT/IL2016/000019 dated Feb. 22, 2017.

International Search Report re: PCT/IL2016/000020 dated Feb. 22, 2017.

Prosulf Package Leaflet: Information for the User. Wockhardt UK Ltd. (2016) 2 pages.

* cited by examiner

HEMOSTATIC MIXTURE OF CELLULOSE-BASED SHORT AND LONG FIBERS

FIELD OF THE INVENTION

The invention relates to a hemostatic composition comprising a mixture of cellulose-based short and long fibers, preparation and use thereof.

BACKGROUND OF THE INVENTION

In a wide variety of circumstances, animals, including humans, can suffer from bleeding due to wounds or during surgical procedures. In some circumstances, the bleeding is relatively minor, and normal blood clotting in addition to the application of simple first aid, are all that is required. In other circumstances substantial bleeding can occur. These situations usually require specialized equipment and materials as well as personnel trained to administer appropriate aid.

Bleeding during surgical procedures may manifest in many forms. It can be discrete or diffuse from a large surface area. It can be from large or small vessels, arterial (high pressure) or venous (low pressure) of high or low volume. It may be easily accessible or it may originate from difficult to access sites.

Conventional methods to achieve hemostasis include use of surgical techniques, sutures, ligatures or clips, and energy-based coagulation or cauterization. When these conventional measures are ineffective or impractical, adjunctive hemostasis techniques and products are typically utilized.

The selection of appropriate methods or products for the control of bleeding is dependent upon many factors, which include but are not limited to bleeding severity, anatomical location of the source, the proximity of source to adjacent critical structures, whether the bleeding is from a discrete source or from a broader surface area, visibility and precise identification of the source and access to the source.

Many products have been developed as adjuncts to hemostasis. These products include topical absorbable hemostats (TAH) such as oxidized regenerated cellulose, gelatin in various forms with or without a thrombin solution, collagen powder, biologically active topical hemostatic products (topical thrombin solutions, fibrin sealants, etc.), and a variety of synthetic topical sealants.

Topical Absorbable Hemostats (TAHs) are widely used in surgical applications. TAHs encompass products based on oxidized cellulose (OC), oxidized regenerated cellulose (ORC), gelatin, collagen, chitin, chitosan etc. To improve the hemostatic performance, scaffolds based on the above materials can be combined with biologically-derived clotting factors such as thrombin and fibrinogen.

One of the most commonly used topical hemostatic agents is SURGICEL® Original absorbable hemostat, made from oxidized regenerated cellulose (ORC). ORC was introduced in 1960 as a safe and effective hemostatic agent for many surgical procedures. SURGICEL® Original is a loose knit ORC fabric that conforms rapidly to its immediate surroundings and is easier to manage than other absorbable agents because it does not stick to surgical instruments and its size can be easily trimmed. This allows the surgeon to hold the cellulose firmly in place until all bleeding stops. The control of bleeding is essential and critical in surgical procedures to minimize blood loss, to reduce post-surgical complications, and to shorten the duration of the surgery in the operating room. Due to its biodegradability and its bactericidal and hemostatic properties, oxidized cellulose, as well as oxidized regenerated cellulose have long been used as a topical hemostatic wound dressing in a variety of surgical procedures, including neurosurgery, abdominal surgery, cardiovascular surgery, thoracic surgery, head and neck surgery, pelvic surgery, and skin and subcutaneous tissue procedures. A number of methods for forming various types of hemostats based on oxidized cellulose materials are known, whether made in powder, woven, non-woven, knitted, and other forms. Currently utilized hemostatic wound dressings include knitted, woven, or non-woven fabrics comprising oxidized regenerated cellulose (ORC), which is oxidized cellulose with increased homogeneity of the cellulose fiber.

SURGICEL® absorbable hemostats are used adjunctively in surgical procedures to assist in the control of capillary, venous, and small arterial hemorrhage when ligation or other conventional methods of control are impractical or ineffective. The SURGICEL® family of absorbable hemostats consists of four main product groups, with all hemostatic wound dressings commercially available from Ethicon, Inc., Somerville, N.J., a Johnson & Johnson Company: SURGICEL® Original hemostat is a white fabric with a pale yellow cast and a faint, caramel like aroma. This material is strong and can be sutured or cut without fraying;

SURGICEL® NU-KNIT® absorbable hemostat is similar to SURGICEL® Original but has a denser knit and thus a higher tensile strength, this material is particularly recommended for use in trauma and transplant surgery as it can be wrapped or sutured in place to control bleeding;

SURGICEL® FIBRILLAR™ absorbable hemostat product form has a layered structure that allows the surgeon to peel off and grasp with forceps any amount of material needed to achieve hemostasis at a particular bleeding site, and therefore, may be more convenient than the knitted form for hard to reach or irregularly shaped bleeding sites. It is particularly recommended for use in orthopedic/spine and neurological surgery.

SURGICEL® SNoW™ absorbable hemostat product form is a structured non-woven fabric that may be more convenient than other forms for endoscopic use due to the structured, non-woven fabric, and is highly adaptable and recommended in both open and minimally invasive procedures.

Another example of a commercial absorbable hemostat containing oxidized cellulose is GELITA-CEL® absorbable cellulose surgical dressing from Gelita Medical BV, Amsterdam, The Netherlands. The commercially available oxidized cellulose hemostat noted above is available in knitted, nonwoven fabrics or powder form. Additional hemostatic products, such as powders consisting of microporous polysaccharide particles and plant starch based particles, are also commercially available as PERCLOT® and ARISTA™.

Background art U.S. Pat. No. 8,815,832; U.S. Pat. No. 3,364,200; US2008/0027365; US2004/0005350; WO2007/076415; U.S. Pat. No. 6,627,749; U.S. Pat. No. 6,309,454; U.S. Pat. No. 5,696,191; U.S. Pat. No. 6,627,749; U.S. Pat. No. 6,225,461; WO2001/024841 A1, EP1,323,436; US2006/0233869.

Howsmon, J. A., & Marchessault, R. H. (1959). The ball-milling of cellulose fibers and recrystallization effects. Journal of Applied Polymer Science J. Appl. Polym. Sci., 1(3), 313-322. doi:10.1002/app.1959.070010308.

Cullen, B., Watt, P. W., Lundqvist, C., Silcock, D., Schmidt, R. J., Bogan, D., & Light, N. D. (2002). The role of oxidised regenerated cellulose/collagen in chronic wound repair and its potential mechanism of action. The International Journal of Biochemistry & Cell Biology, 34(12), 1544-1556. doi:10.1016/s1357-2725(02)00054-7.

Rajkhowa, R., Wang, L., & Wang, X. (2008). Ultra-fine silk powder preparation through rotary and ball milling. Powder Technology, 185(1), 87-95. doi:10.1016/j.powtec.2008.01.005.

Yasnitskii, B. G., Dol'berg, E. B., Oridoroga, V. A., Shuteeva, L. N., Sukhinina, T. V., & Bogun, T. A. (1984). Oxycelodex, a new hemostatic preparation. Pharmaceutical Chemistry Journal, 18(4), 279-281. doi:10.1007/bf00760712.

SUMMARY OF THE INVENTION

The present invention relates to improved hemostatic compositions comprising a mix of short and long fibers originated from a cellulose-based material.

In one aspect, the invention relates to hemostatic fibers and/or aggregates composition comprising long and fine cellulose-based fibers, wherein the long and the fine fibers are at a ratio in the range of 5%-25% w/w and 95%-75% w/w, respectively; wherein the size distribution of the long fibers is: D90 of more than 177 µm and D50 of more than 95 µm, and wherein the size distribution of the fine fibers is: D90 of less than 177 µm, and D50 of less than 95 µm. All percentages are w/w of the entire weight composition.

In some embodiments of the invention, the D90 of the long fibers is less than 350 µm and the D50 is less than 167 µm.

In some embodiments of the invention, the hemostatic composition further comprises at least one compound selected from the group consisting of:
  a) a divalent cation selected from zinc, calcium, magnesium, manganese, and copper;
  b) a positively charged peptide and/or polysaccharide;
  c) an omega amino carboxylic acid; and
  d) a combination of any of the above.

In one embodiment, the composition comprises an omega amino carboxylic acid at a concentration range of 2.5%-5.0% w/w of the entire composition; protamine salt at a concentration range of 2.5%-5.0% w/w of the entire composition; a divalent cation salt, the cation concentration in the salt being 1.3%-1.8% w/w of the entire composition. The remaining weight is contributed by the cellulose-based fibers to a total weight of 100% w/w.

In some embodiments of the invention, the hemostatic composition further comprises protamine salt, calcium chloride, and ε-aminocaproic acid (εACA). The remaining weight is contributed by the cellulose-based fibers to a total weight of 100% w/w.

In one embodiment, the concentration ranges of εACA, protamine sulfate, and calcium chloride are 2.5%-5.0%, 2.5%-5.0%, 5.0%-6.5% w/w, respectively. The remaining weight is contributed by the cellulose-based fibers to a total weight of 100% w/w.

The composition comprises long fibers at a concentration in the range of 5%-25% w/w. The remaining weight is contributed by the short fibers (present at a concentration range of 75%-95%), and optionally other compounds/additives, to a total weight of 100%.

In some embodiments of the invention, the cellulose-based fibers are oxidized regenerated cellulose fibers.

In some embodiments of the invention, the hemostatic composition being in the form of aggregates having a size in the range of 75-420 µm.

In another aspect, the invention relates to a method of making a hemostatic composition comprising the steps of:
  a) reducing a size of a cellulose-based material, e.g. a fabric, to form long fibers and fine fibers, wherein the size distribution of the long fibers is: D90 of more than 177 µm and D50 of more than 95 µm, and wherein the size distribution of the fine fibers is: D90 of less than 177 µm, and D50 of less than 95 µm; and mixing the long and fine fibers at a ratio in the range of 5%-25% w/w and 95%-75% w/w, respectively, thereby obtaining a hemostatic fibers composition.
  b) Optionally the hemostatic fibers composition obtained in step a) is subjected to further steps to obtain a hemostatic composition in the form of aggregates.

In some embodiments of the invention, aggregates are formed in steps comprising:
  i) compacting the hemostatic fibers composition to obtain compacted hemostatic fibers composition; and
  ii) reducing the compacted composition size.

In some aspects the invention relates to a method of making a hemostatic composition comprising the steps of:
  a) reducing the size of a cellulose-based material to form long fibers and fine fibers, wherein the size distribution of the long fibers is: D90 of more than 177 µm and D50 of more than 95 µm, and wherein the size distribution of the fine fibers is: D90 of less than 177 µm, and D50 of less than 95 µm; and mixing the long and fine fibers at a ratio in the range of 5%-25% w/w and 95%-75% w/w, respectively, thereby obtaining a hemostatic fibers composition.
  b) Optionally, the hemostatic fibers composition obtained in step a) is subjected to further steps to obtain a hemostatic composition in the form of aggregates, the steps comprising: i) compacting the hemostatic fibers composition to obtain compacted hemostatic fibers composition; and optionally ii) reducing the compacted composition size.

In some embodiments of the invention, the D90 of the long fibers is less than 350 µm and the D50 is less than 167 µm.

In some embodiments of the invention, reducing the size is carried out by milling.

In some embodiments of the invention, reducing the size in step a) is preceded by a step of slitting and/or cutting the cellulose-based material.

In some embodiments of the invention, reducing the size in step a) is a two-part process, and wherein the second part is carried out in an air classifier mill.

In some embodiments of the invention, the milling in the air classifier mill is carried out one time (one pass) for obtaining the long fibers and three times (three passes) for obtaining the fine fibers.

In some embodiments of the invention, the compacting step i) is preceded by a step of humidifying the hemostatic fibers composition, optionally to a water content level of between 11% and 18% by weight.

In some embodiments of the invention, the step of humidifying is carried out by including in the hemostatic fibers composition a hygroscopic material, optionally calcium chloride.

In some embodiments of the invention, reducing the size in step ii) is preceded by a step of dehumidifying the compacted composition.

In some embodiments of the invention, the dehumidifying is carried out to a water content level of less than 5% by weight.

In some embodiments of the invention, the compacting in step i) is carried out using a slugging machine, optionally at a force in the range of 25-70 kN/cm.

In some embodiments of the invention, obtaining hemostatic aggregates in step b) is targeted to produce aggregates having a dimension in the range of 75-420 µm.

In some embodiments of the invention, the cellulose-based material is oxidized regenerated cellulose fabric, oxidized regenerated cellulose non-woven fabric, oxidized regenerated cellulose woven fabric, oxidized regenerated cellulose knitted fabric, shredded oxidized regenerated cellulose material or combinations thereof In some embodiments of the invention, the method further comprises adding to the long and fine fibers at least one compound selected from the group consisting of:
a) a divalent cation selected from zinc, calcium, magnesium, manganese, and copper;
b) a positively charged peptide and/or polysaccharide;
c) an omega amino carboxylic acid; and
d) a combination of any of the above.

In some embodiments of the invention, the method further comprises adding to the long and fine fibers protamine salt, calcium salt, and ε-aminocaproic acid.

In another aspect, the invention relates to a hemostatic composition in the form of fibers and/or aggregates obtainable according to the method of the invention.

In another aspect, the invention relates to a method for forming a gel comprising the step of: contacting a hemostatic composition in the form of fibers and/or aggregates according to the invention with blood, thereby forming a gel.

In another aspect, the invention relates to a gel obtainable by the method according to the invention.

In another aspect, the invention relates to a kit comprising a container including a hemostatic composition in the form of fibers and/or aggregates according to the invention and optionally an applicator, a carrier and/or instructions for use.

In some embodiments, the container is an applicator.

In another aspect, the invention relates to a method of treating a bleeding wound, a bacterial infection at a wound site, for sealing a leak at a site, preventing adhesion at a site, and/or minimizing or preventing a leak from an anastomotic site in a subject in need, the method comprising the step of: applying an effective amount of the hemostatic composition according to the invention in the form of fibers and/or aggregates onto and/or into the wound and/or site of the subject.

The invention relates to the use of a hemostatic composition in the form of fibers and/or aggregates according to the invention, as an anti-bactericidal agent, to stop bleeding, for sealing, preventing adhesions, and/or minimizing or preventing leaks from anastomotic sites. In some embodiments, the use is for minimizing or preventing leaks in a coronary artery bypass graft (CABG) surgery.

In one embodiment the application is carried out without applying pressure on the composition towards the wound and/or site. For example, manual compression using a gauze is not necessary. In various products the product requires manual compression during application for at least a minute. The advantage of using the hemostatic composition without compression is that the hemostatic composition can be applied in/on hard to reach areas.

DETAILED DESCRIPTION

Figure 1:
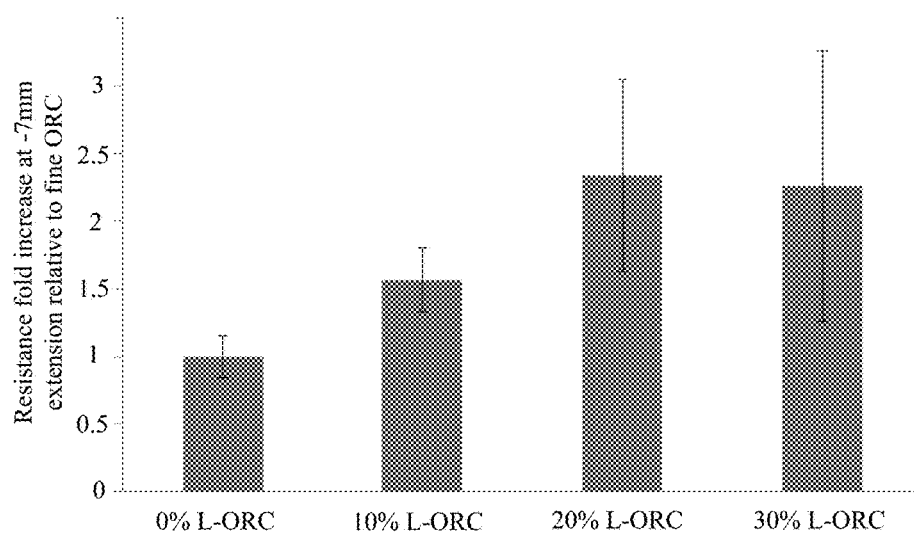
FIG. 1 is a bar diagram showing the resistance force/cohesive strength obtained for the different fiber compositions using a modified Bloom test. The resistance force obtained from non-supplemented fine ORC fibers served as a baseline for the entire experiment. The addition of long ORC fibers (L-ORC) was shown to increase the clots resistance.

The invention relates to fibers and/or aggregates composition(s) having surprising physical properties and highly beneficial effect(s) for hemostasis upon gel or clot formation; to their preparation and use thereof. The hemostatic composition comprises a mix of short and long fibers originated from a cellulose-based material in the form of fibers and/or aggregates. For example, the fibers and/or aggregate composition induce gel or clot formation having beneficial physical properties, such as increased cohesive strength, and beneficial hemostatic capability.

The term "cellulose-based fibers" relates to fibers comprising a cellulose backbone. The cellulose backbone can be modified, for example, it may include alterations in carboxylation or oxidation levels. Non limiting examples of cellulose-based materials include oxidized cellulose or oxidized regenerated cellulose, Carboxymethyl cellulose, Hydroxyethyl cellulose, Hydroxypropyl cellulose and Methylcellulose.

Cellulose-based materials can be woven, non-woven, knitted, and/or other forms of fabrics.

Non limiting examples of cellulose-based fibers are ORC fibers, Cotton fibers, Rayon fibers, and Viscose fibers.

The term "fibers" relate to structures having elongated threadlike form.

The hemostatic fibers composition can be in the form of powder.

In one embodiment of the invention, the "fine or short" cellulose-based fibers in the composition have a size distribution of D90 of less than 177 µm, and D50 of less than 95 µm.

In one embodiment of the invention, the "long" cellulose-based fibers in the composition have a size distribution of D90 of more than 177 µm and D50 of more than 95 µm. In another embodiment, the long fibers have a size distribution of less than 350 µm and the D50 is less than 167 µm.

Size distribution D50 is also known as the median diameter or the medium value of the units in the powder/aggregates size distribution, it is the value of the units' diameter at 50% in the cumulative distribution. For example, if D50 is X µm, then 50% of the units in the sample are larger than X µm, and 50% are smaller than X µm. Size distribution is the number of units that fall into each of the various size ranges given as a percentage of the total number of all units' sizes in the sample of interest. Accordingly, D90 value refers to 90% of the units having a size that is smaller than the D90 value.

The term "powder" relates to dispersed dry solid particles.

The term "aggregates" relates to compacted cellulose-based material having a target size range e.g. the compacted material is subjected to size reduction such as milling and optionally sieving.

Non limiting examples of size reduction are tearing, shredding, milling, grinding, and/or sieving.

In one embodiment aggregates are compacted fibers composition subjected to size reduction such as milling.

The term "hemostatic" relates to the ability to reduce bleeding intensity or to arrest bleeding.

The results are based on the following findings:

It was found according to the invention that the hemostatic composition according to the invention exhibit superior properties when compared to a comparative composition of fine cellulose-based fibers.

It was found that supplementing fine ORC fibers with long ORC fibers increased the clots' resistance and cohesive strength.

The results show that mixture of fine ORC fibers with long ORC fibers increased the cohesive strength of a clot formed upon contact with blood by at least 1.5 times.

The term "resistance of a gel or clot" relates to the results of the modified bloom test (as exemplified below) that demonstrate the force required by the metallic rod to pass through the gel at extension of 7 mm whilst moving at a speed of 5 mm/min. This force reflects the level of resistance of the gel (the greater the force, the greater the resistance of the gel) and in turn indicates the level of cohesive strength of a gel. The greater the force required for the rod to precede with its steady movement, the greater the resistance of the gel.

It was found herein that use of ORC fibers with different size distributions can increase the resulting structural integrity of the clot produced following application of the fibers and/or aggregates.

It was also found that supplementation of short ORC fibers with long ORC fibers could improve the hemostatic capabilities of the composition nearly by a two fold increase relative to a non-supplemented fine ORC fibers-including composition having long fibers in a concentration of less than 25% of the total composition weight.

Also, supplementation of fine ORC fibers with long fibers and all three following compounds calcium chloride, PS and εACA exhibited superior results. The positive effect was observed at a specific ratio of the supplements.

A composition comprising 80% fine ORC fibers with 10% long ORC fibers and including 5% $CaCl_2$, 2.5% PS, and 2.5% εACA exhibited superior hemostatic results, of two folds, as compared to a composition consisting of fine ORC fibers.

The fibers and/or aggregates composition comprising oxidized regenerated cellulose (ORC) fibers including a mixture of fibers with different size distribution exhibits superior properties when compared to a composition including ORC fibers prepared only with fine fibers.

Without being bound by the mechanism, the cellulose-based fibers mixture having different size distribution, and optionally the compound(s), contribute to the structure of the clot achieved in-situ.

In one aspect the invention relates to fibers and/or aggregates composition comprising long and fine cellulose-based fibers, wherein the long and the fine fibers are at a ratio in the range of 5%-25% w/w and 95%-75% w/w, respectively, wherein the size distribution of the long fibers is: D90 of more than 177 μm and D50 of more than 95 μm, and wherein the size distribution of the fine fibers is: D90 of less than 177 μm, and D50 of less than 95 μm.

Where applicable, all ranges disclosed herein include the upper and lower limit.

In some embodiments, the long fibers are at concentration in the range of 5% to less than 25%.

Oxidized regenerated cellulose materials that can be used as a starting material for making the hemostatic composition of the present invention are known and commercially available. The starting materials can include absorbable woven or knitted fabric or non-woven materials comprising oxidized polysaccharides, in particular oxidized cellulose and the neutralized derivatives thereof. For example, the cellulose may be carboxylic-oxidized or aldehyde-oxidized cellulose. More preferably, oxidized regenerated polysaccharides including, but without limitation, oxidized regenerated cellulose may be used. Oxidized regenerated cellulose is preferred due to its higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents of each of which are hereby incorporated by reference as if set forth in its entirety.

Examples of preferred cellulose-based materials that may be utilized include, but are not limited to, INTERCEED® absorbable adhesion barrier, SURGICEL® Original absorbable hemostat, SURGICEL® NU-KNIT® absorbable hemostat, SURGICEL® FIBRILLAR™ absorbable hemostat, SURGICEL® SNoW™ absorbable hemostat. Hemostatic fibers and/or aggregates of the present invention can perform as a hemostat in either a paste or powder form with superior hemostatic properties and good tissue conformability and flowability. In addition, hemostatic fibers and/or aggregates can be physically incorporated and/or mixed with other agents and biopolymers to improve adherence to tissues, sealing properties, and/or anti-adhesions properties.

In one aspect of the present invention, there is provided a method for making hemostatic fibers and/or aggregates composition having beneficial hemostatic, wound healing, and other therapeutic properties.

One possible method of the present invention comprises manufacturing hemostatic fibers and/or aggregates directly from cellulose-based materials, such as ORC products e.g. those discussed above.

In one embodiment, long and short fibers are obtained by reducing the size of a cellulose-based material, long fibers can be obtained by including less milling steps and/or shorter milling time as compared to the steps and/or time required to obtain the fine fibers.

In an alternative embodiment, the cut cellulose-based fabric pieces are converted directly into fine fibers in a ball mill. Different number of rounds and or milling time periods in the ball mill results in different fiber sizes. Larger fibers taken from the ball milling step could be collected for future use in order to incorporate different fiber sizes in the final fibers and/or aggregates composition(s).

Cellulose-based fine fibers obtained after milling can be mixed with long cellulose-based fibers previously obtained, and optionally can be further mixed with compound(s) and/or additives, e.g. to improve adherence to tissues, sealing properties, hemostasis properties, and/or anti-adhesions properties.

Mixing the long and fine fibers can be carried out at a ratio in the range of 5%-25% and 95%-75%, respectively, wherein D90 of the long fibers is more than 177 μm and D50 is more than 95 μm and wherein D90 of fine fibers is less than 177 μm and D50 is less than 95 μm.

The produced hemostatic fibers composition can be further supplemented with a compound.

In one embodiment, the method of making the hemostatic composition starts with cellulose-based material, such as ORC material, e.g. SURGICEL® Original absorbable hemostat. ORC fabric is cut into 2.54-5.08 cm (1- to 2-inch) wide sections before the material is fed into a blade that cuts the fabric into smaller pieces. The cut ORC fabric pieces are then ground into ORC fibers by two consecutive milling processes (hammer milling and air classifier milling). The fibers from different milling steps are taken for future use, in order to incorporate different fiber sizes in the final fibers composition(s). The obtained hemostatic fibers composition can be subjected to further steps to obtain a hemostatic composition in the form of aggregates.

In some embodiments, the term different fiber sizes relates to fibers having different size distribution.

In one embodiment, the cellulose-based fibers in the composition are comprised of a mixture of cellulose-based fibers with different size distribution. The cellulose-based fibers mixture can be further mixed with a compound(s). In one embodiment, the mixture can go through a process of compaction and milling to form aggregates. The aggregates of cellulose-based fibers, optionally with the compound(s) can range from 75 µm to 420 µm.

In one embodiment, prior to forming aggregates, cellulose-based fibers mixture containing the long and fine fibers, are subjected to a humidification step to a level of about 11% and about 18%, to about 11% to about 16%, most preferably about 12-16% (measured by Ohaus halogen moisture analyzer) for the subsequent processing. This step could be omitted if a sufficient amount of hygroscopic material, such as calcium chloride, is added to the fibers. Sufficient amount of hygroscopic compound is, for example, an amount that allows humidification to a level of about 11% to about 18% as measured by Ohaus halogen moisture analyzer. The resulting moist mixed fibers are then compacted.

The term "hygroscopic material" relates to a substance that is capable of attracting and holding water molecules from the surrounding, usually at normal or room temperature environment. Non limiting examples include zinc chloride, calcium chloride, potassium hydroxide and sodium hydroxide.

In one embodiment, forming aggregates include a step of dehumidification or drying process, after compaction and before size reduction, and include a sieving step. The size reduction and sieving step typically allows targeting aggregates having a certain dimension. The next steps can be dosing into applicator devices and then subjecting the device to packaging and sterilization.

In one embodiment, storage moisture prior to dosing into an applicator is less than about 2% w/w at conclusion of drying to achieve less than 6% w/w moisture content in controlled environment (0.3-0.6%/hr per 500 gram sample moisture gain depending on relative humidity, commonly 25-55% relative humidity) for dosing into applicators. One possible method for making the hemostatic composition(s) comprises the steps of: slitting and cutting of cellulose-based material; reducing the size e.g. by milling the resulting material; milling step(s) in an air classifier for obtaining long and fine fibers; mixing fibers of the different sizes and optionally adding the compound(s).

Another possible method for making the hemostatic composition(s) comprises the steps of: slitting and cutting of cellulose-based material; reducing the size e.g. by milling the resulting material; milling step(s) in an air classifier for obtaining long and fine fibers; mixing fibers of the different sizes, and optionally adding the compound(s); humidification (could be omitted in case that a sufficient amount of hygroscopic material [e.g. calcium chloride] is added); compaction; dehumidification or drying; reducing the size of the compacted material; sieving; optional dosing into storage containers or into delivery devices, primary packaging and secondary packaging; and optional sterilization.

Slitting and cutting can be carried out to slit and cut fabric into appropriate size pieces that are between approximately 2.54 cm by 7.62 cm or 5.08 cm by 7.62 cm (1 inch by 3 inches or 2 inches by 3 inches), though smaller pieces can also be used. The main operations performed for slitting and cutting are to unwind a roll of fabric, slit the fabric into strips, cut the strips to size and deliver the cut pieces into the first milling step. A number of cutting and slitting machines are known and commercially available, such as AZCO Model FTW-1000 available from AZCO.

In a first milling step, processed pieces of cellulose-based fabric material are converted from an intermediate coarse fiber produced in the slitting and cutting step to a material having a D90 value of less than 452 µm and D50 value of less than 218 µm, while having minimal impact on the color index and water soluble content of the material. A number of machines for milling are commercially available, such as Models DASO6 and WJ-RS-D6A manufactured by Fitzpatrick, which are hammer mill type milling machines, equipped with a 497 µm round screen and a set of blades that breaks down the fabric until it passes through the screen to produce intermediate coarse cellulose fiber. In an exemplary processing run, mill speed can be about 7000 RPM; processing temperature at less than 80° C.; number of blades as 8 (2 impellers each); blade type as a 225 knife, impact type blades; blade orientation set as "impact".

Fiber produced in a milling step can be further reduced while keeping a minimal impact on the color index and water soluble content of the material. A number of machines are available for second milling step, such as an Air Classifier/F10 Quadro Fine Grind from Quadro.

Intermediate coarse fiber from the first milling step can be fed at a controlled rate into the second mill and passed through two milling chambers that are separated by a milling screen. The material can be pulled through the milling chamber by an air blower. The intermediate coarse fiber can be processed through the air classifier equipment several times in order to obtain the desired size. In addition, fibers could be taken from these milling steps for future use in order to incorporate different fiber sizes in the final fibers and/or aggregates. Intermediate coarse fibers from the first milling step can be fed at a controlled rate into the second mill. The intermediate coarse fibers can be processed through the air classifier equipment three times in order to obtain the desired size. In addition, in certain experiments, fibers taken from the first run through the air classifier can be extracted in order to incorporate different fiber sizes in the final aggregates.

In an embodiment, fibers collected from the first and third run through the air classifier is used for making improved fibers/aggregates composition.

At this step(s), a Quadro Air Classifier F10 can be used with a milling speed of 8400 rpm, blower speed of 1800 rpm and 3 passes. In such an embodiment, after one pass, the resulting long fibers can have a D90 value of less than 350 µm and a D50 value of less than 167 µm. After 3 passes, the resulting fine fibers can have a D90 value of less than 177 µm and a D50 value of less than 95 µm.

Fine fiber can also be produced in one step by ball milling instead of in two milling steps as described above.

In an alternative ball milling embodiment, 50 g of pre-cut cellulose-based fabric [e.g. ORC fabric] (5×5 cm or 2"×2") is ball milled with 12 high-density Zirconia (zirconium dioxide ZrO2, 20 mm in diameter; Glen Mills Inc., Clifton, N.J., USA) by placing the balls and the samples in a 500 mL grinding jar. The jar is clamped into the latching brackets and then counterbalanced on the planetary ball mill PM100; Retsch, Inc., Newtown, Pa., USA). The milling is then performed bi-directionally at 450 rpm for 20 minutes. By using different milling parameters such as time, different fibers size could be produced which could be used for future incorporation in the mix that could result in improved aggregates.

In one embodiment, the humidity chamber suitable for the humidification step is commercially available as Model CEO-916-4-B-WF4-QS by Thermal Product Solutions. Humidification of chamber air is achieved by water vapor injection. The typical steady-state temperature of 25° C. can be utilized, while the humidity level can be cycled between 75% and 85%, with a preferred target of 85% air humidity. Humidification time or residence time of the material inside the humidity chamber can range from several hours to several days depending on the quantity of the material and air recirculation. In a typical and preferred cycle, the material will have 12-13 hours residence time for about 3,000 grams of cellulose fine fiber arranged in several trays and exposed to 85% relative humidity and a target of 12% moisture content of the fibers after humidification.

In one embodiment the fine fibers are mixed with long fibers, and optionally with compounds and/or additives prior to compaction.

The compressed material can be milled and sieved and aggregates between 75-420 μm can be collected.

Compaction equipment is known and commercially available. Fibers could be compacted by slugging machinery or any other compaction technique known in the art. Exemplary compaction units are the Fitzpatrick Chilsonator IRR220-L1A with Retsch manual sieving AS200 Screener and the Fitzpatrick Chilsonator CCS220/M3B & RV-M5A with Screener Sweco Vibro-energy unit integrated under M5A. The compaction processing can be performed using two separate subsystems that are bound by a common electrical system. For example, a first subsystem (Roller Compactor: main unit) can be the Fitzpatrick Chilsonator CCS220 roller compactor and the M3B mill for pre-breaking the compacted material, while the second subsystem (Roller Compactor: secondary milling unit) is M5A mill for the final milling with a Sweco or Retch screener for the separation to obtain the desired size aggregates.

Moisture can be removed following compaction in a dehumidification or drying step. The dehumidification or drying step preferably does not significantly affect any other product quality attributes, such as color, bulk density, water soluble content and size. Typically, the fibers can be dried as a batch using a conventional fluidized air bed.

Dehumidification equipment is known and commercially available. An exemplary bench-top fluidized air bed is commercially available from Retsch (TG-200) with 6 L capacity. Alternatively, a fluidized bed Model No. 0002 from Fluid Air (Aurora, Ill.) can also be used.

In some embodiments of the invention, one or more polysaccharides having positive charges are further added/included in the compositions according to the invention. Non limiting examples of polysaccharides having positive charges are chitosan and cationic guar gum.

In some embodiments of the invention, one or more peptides having positive charges are further added/included in the compositions according to the invention. Non limiting examples of such peptides are: abaecin, apidaecins, prophenin, indolicidin, melittin, magainins, LL-37, Bovine lactoferricin, Human lactoferricin, Cecropin A1, Buforin II, Thanatin, Polyphemusin 1, Magainin 2, Human β-defensin-2, Rabbit kidney defensin. Penetratin/Antenapedia, TAT, SynB1, SynB3, PTD-4, PTD-5, FHV Coat-(35-49), BMV Gag-(7-25), HTLV-II Rex-(4-16), D-Tat, R9-Tat Transportan, MAP, SBP, FBP, MPG, MPG(ΔNLS), Pep-1, Pep-2.

In a further aspect, the invention provides a method for forming a gel, the method comprising the step of: contacting a hemostatic composition according to the invention with blood, thereby forming a gel.

The term "blood" includes blood fractions such as plasma.

The term "gel" relates to a viscous and/or solid-like material that can have properties ranging from soft and weak to hard and tough. The gel can be a hydrogel.

Typically, a hydrogel is a network of polymer chains that are hydrophilic. Hydrogels can contain over 90% water and include polymeric networks.

The gel can be a clot being a thick mass of coagulated liquid, especially blood.

The term "contacting" is used in its broadest sense and refers, for example, to any type of combining action which brings the hemostatic composition into sufficiently close proximity with the blood such that a clot or gel is formed.

In one embodiment, the method forms a gel having a resistance of equal to or more than 1.5 times higher than that of a gel formed upon contact of a comparative composition with blood, and/or forms a gel having a hemostatic capability of about two fold or higher than that of a gel formed upon contact of a comparative composition with blood, wherein the comparative composition comprises fine cellulose-based fibers and lacks the cellulose-based long fibers.

In a further aspect, the invention provides a gel obtainable by the method of the invention.

In a further aspect, the invention provides a kit comprising a container including a hemostatic composition of the invention, and optionally an applicator or carrier, and optionally instructions for use.

The term "carrier" relates to a physical matrix comprising and/or holding the hemostatic composition. Examples of carriers include, but are not limited to, pads for internal and/or external use such as cellulose-based pads, collagen-based pads; implants such as orthodontic and orthopedic implant; flowable sealants and/or hemostats such as SURGIFOAM®, EVICEL®.

In one embodiment hemostatic fibers and/or aggregates composition according to the present invention are made from oxidized cellulose-based (ORC) fiber materials or from pre-shredded oxidized cellulose (OC)-based materials.

The resulting hemostatic fibers and/or aggregates composition can be used for various surgical and/or wound healing topical applications, such as for anti-bactericidal treatment, hemostasis, anti-adhesion, sealing, and/or for minimizing or preventing leaks e.g. leaks from anastomotic sites such as leaks created during coronary artery bypass graft (CABG).

The composition may be used to stop bleeding in hard to reach areas e.g. during laparoscopic surgery, on anastomotic sites such as CABG and/or arteriovenous anastomosis, procedures where applying pressure is unwarranted such as spinal surgery or neuronal surgery.

Patients that undergo coronary artery bypass graft (CABG) surgery may have leaks from the anastomotic sites created during the procedure. Many of these leaks are addressed during the surgery using either additional sutures or various hemostats. Stopping these leaks during surgery and preventing them from developing post operatively, will help surgeons be more confident that their patients will not have post-operative anastomotic leaks. Bleeding after CABG procedures requiring a transfusion or reoperation is associated with a significant increase in morbidity and mortality. In as many as 20% of cases, a specific site of bleeding can be identified, during the reoperation. The typical sources of surgical bleeding include cannulation sites, the proximal and distal anastomotic site, and the branches of the ITAs and vein grafts. According to literature, 2-3% of CABG patients will require re-exploration for bleeding and as many as 20% will have excessive post-operative bleeding requiring blood transfusion.

The hemostatic composition(s) may have one or more of the following advantages over several known products:

1—can stop bleedings e.g. at large blood vessels suture line and therefore can significantly reduce and stop bleeding from blood vessels suture lines unlike several known products which have limited efficacy in achieving hemostasis in blood vessels;

2—can achieve hemostasis without the need for pressure application. Several known products require the application of pressure (e.g. manually compressing with a gauze) in order to achieve hemostasis;

3—is activated in blood. When activated by moisture, the hemostatic fibers and/or aggregates gain structure (e.g. in the form of a clot/gel) and can achieve hemostasis. Several known products have pre-formed structural integrity;

4—can set in blood, does not float away easily and can achieves hemostasis. Several known products have limited efficacy in a wet environment;

5—can adhere to the bleeding site, yet still reversible i.e. adheres to the bleeding site and resists lavage, yet can be scraped off to remove and gain access if surgical correction is needed. Several known products have either limited adherence in a wet field or they cannot be easily removed once applied.

The content of all cited publications are hereby incorporated by reference in their entirety.

EXAMPLES

Material and Methods.

TABLE 1A

Oxidized Regenerated Cellulose (ORC) Fibers.

| Oxidized Regenerated Cellulose (ORC) Fibers | Category |
|---|---|
| Long ORC Fibers<br>Distribution: D90 of more than 177 μm and D50 of more than 95 μm* | Cellulose-based fibers |
| Fine ORC Fibers<br>Distribution: D90 of less than 177 μm, and D50 of less than 95 μm* | Cellulose-based fibers |

*See below elaboration on the preparation.

TABLE 1B

Compounds Used to Supplement ORC Fibers.

| Compound | Category | Manufacturer | Cat. Number |
|---|---|---|---|
| Calcium Chloride dihydrate | Divalent cation salt | Merck | 1.42000.5000 |
| Protamine Sulfate (PS) | Protamine salt | Sigma | P3369-100G |
| 6-Aminocaproic acid (ε-aminocaproic acid = epsilon-aminocaproic acid = εACA) | Omega amino carboxylic acid | Sigma | A204-100G |

Table 2 shows the percentage (w/w based on the entire weight composition) of cations in $CaCl_2$ used in the experiments.

TABLE 2

% (w/w) of Cation Concentration Equivalent in $CaCl_2$.

| Amount of Indicated Salt (w/w) | Amount of Calcium Cations (w/w) |
|---|---|
| 3.0% $CaCl_2$ | 0.818% |
| 3.5% $CaCl_2$ | 0.954% |
| 5.0% $CaCl_2$ | 1.363% |
| 6.0% $CaCl_2$ | 1.636% |
| 6.5% $CaCl_2$ | 1.768% |

Oxidized Regenerated Cellulose (ORC) Fibers Preparation.

The manufacturing process of the ORC fibers started with ORC material SURGICEL® Original absorbable hemostat. ORC material was cut into 2.54-5.08 cm (1- to 2-inch) wide sections before the material was fed into a blade that cuts the fabric into smaller pieces. The cut ORC fabric pieces were then ground into ORC fine fibers by two consecutive milling processes (hammer milling and air classifier milling). The fibers from different milling steps were taken for future use in order to incorporate different fiber sizes in the final aggregates.

More specifically, the process for manufacturing the fibers comprised the steps of: slitting and cutting of SURGICEL® Original fabric; milling the resulting material using hammer milling; milling step(s) in an air classifier for obtaining long and fine fibers; and optionally mixing fibers of the different sizes.

Slitting and cutting was carried out to slit and cut fabric into appropriate size pieces that are approximately 2.54 cm by 7.62 cm (1 inch by 3 inches). The main operations performed for slitting and cutting were to unwind a roll of fabric, slit the fabric into strips, cut the strips to size and deliver the cut pieces into the first milling step.

In a first milling step, processed pieces of cellulose-based fabric material were converted from an intermediate coarse fiber produced in the slitting and cutting step to a material having a D90 value of less than 452 μm and D50 value of less than 218 μm, while having minimal impact on the color index and water soluble content of the material. The machine used for milling at this step was a hammer mill type model WJ-RS-D6A manufactured by Fitzpatrick. The hammer mill was equipped with a 497 μm round screen and a set of blades that breaks down the fabric until it passes through the screen to produce intermediate coarse cellulose-based fiber. The parameters of the milling were: mill speed of about 7000 RPM; processing temperature of less than 80° C.; number of blades of 8 (2 impellers each); blade type of a 225 knife, impact type blades; blade orientation set as "impact".

Intermediate coarse fibers from the first milling step were fed at a controlled rate into the second mill. The intermediate coarse fibers were processed through the air classifier equipment three times in order to obtain the desired size. In addition, in certain experiments, fibers taken from the first run through the air classifier were extracted in order to incorporate different fiber sizes in the final aggregates.

At this step(s), a Quadro Air Classifier F10 was used with a milling speed of 8400 rpm, blower speed of 1800 rpm and 3 passes. After one pass, the resulting long ORC fibers had D90 of more than 177 μm and D50 of more than 95 μm. After 3 passes, the resulting fine ORC fibers had a D90 value of less than 177 μm and a D50 value of less than 95 μm.

Powder Composition Preparation.

All powders were weighed using an analytical balance in humidity controlled conditions. Relative humidity did not exceed 20% throughout the powder preparation process. All powders were comprised of ORC fine fibers having D90 of less than 177 μm and D50 of less than 95 μm, prepared as described above (Table 1A), and supplemented with long ORC fibers having: D90 less than 350 μm and D50 of less than 167 μm in the ratios specified in each Example. All powder compositions in Example 2 were also supplemented with 5% $CaCl_2$, 2.5% PS and 2.5% εACA. For example, in Example 2 and FIG. 2 the composition named 10% L-ORC consisted of 80% fine ORC fibers, 10% long ORC fibers, 5% $CaCl_2$, 2.5% PS and 2.5% εACA. All percentages are w/w of the entire weight composition.

All compounds, elaborated in the Table 1B, were provided in powder form.

Each powder mixture was transferred to a mortar and pestle and mixed thoroughly until the powder particles were equally/homogenously distributed within the composition. To minimize adsorption of humidity, the powder compositions were stored in vials and sealed with a plastic paraffin film (PARAFILM®).

Aggregate Preparation.

To obtain aggregates/granules that contain a higher mass per volume ratio, two steps were carried out:
I—Powder compaction (capsulation); and
II—Capsule drying, milling/grounding and sieving.
See elaboration of steps I and II below.

Powder Compaction.

Compaction was carried out using a manual hydraulic press (Specac Atlas 15 tons model GS15011) and a suitable evacuable pellet die, the pellet die has a diameter of 10 mm (Specac GS03100). About 300 mg powder composition (prepared as described above) was loaded into the pellet die up to a height of approximately 1.5-2.0 cm. In the next step, a metallic rod (which is part of the manual hydraulic press equipment) was fitted on top of the powder and used to reach a pressure of 4 tons (about 1.3 tons per $cm^2$) by the manual hydraulic press. Following this step, a capsule (compacted powder) in a diameter of 10 mm and a height of approximately 0.3-0.5 cm was formed. The capsule was released from the pellet die and broken into halves with a mortar and pestle to increase surface area for the next drying step.

Capsule Drying, Milling/Grounding and Sieving.

Capsule halves were dried in a vacuum oven (Cole Parmer vacuum oven model 05017-05) at 37° C. for approximately 16 hours to remove any excess humidity (and reach a humidity of less than 5% w/w) and enable milling of the capsules. The dried capsule halves were ground/milled at 20,000 rpm for 30 seconds using IKA® Works, Inc. tube mill control 9737790. In the next step, the powder was vigorously sieved using an MRC (sieve manufacturer) sieve shaker (model LS-200 at an intensity level 2) for 1 minute through a set of 2 sieves; one with a pore size of 420 μm and another with a pore size of 75 μm. The aggregates remaining between the two sieves was collected and stored at room temperature (20-27° C.) in a tightly closed vial, sealed with plastic paraffin film until use. At the end of this stage, all components were present in each final granule/aggregate composition and were homogenously distributed within it.

The compositions in Example 1 were in powder form and the compositions in Examples 2 and 3 were in aggregate form.

Blood Preparation.

The blood used in the experiment 1 was collected from exterminated Porcines by Lahav contract research organization (C.R.O.) and delivered in chilled containers (4° C.). Upon blood collection, 5000 IU Heparin was added per liter of blood [Heparin Sodium-Fresenius 5000 IU/1 ml solution for injection; manufacturer: BODENE (PTY) LTD trading as Intramed; Cat. Number: 9207910LAB].

To prevent clotting, upon arrival additional Heparin was added (5000 IU per 1 liter blood). The heparinized blood was mixed gently by inverting the bottle several times. In the next step, to remove residual clots, the heparinized blood was filtered through a 20 μm polypropylene syringe filter (SVL25D20HQSA25 by Entegris) and collected into a polypropylene container (to prevent blood clotting induced by glass). The filtered heparinized blood was stored at 4° C. until use.

Bloom Test.

Bloom is a test used to measure the cohesive strength of a gel or gelatin. Cohesive strength represents the bonding between the molecules of a tested material/composition. Generally, Bloom test relates to determination of the force (in grams) which has to be applied to a free surface of 6.67% gelatin gel (prepared by dissolving 7.5 g gelatin in 105 g water) by means of a cylindrical piston (having a diameter of 12.7 mm) in order to produce a depression of 4 mm. For the test, the gel is typically formed in a glassware with the following dimensions: a capacity of 150 ml, an interior diameter of 59 mm, and a height of 85 mm. The speed of the descending piston is set to 30 mm/minute (see Bloom Test described in U.S. Pat. No. 1,540,979).

In the Examples below, a modified Bloom Test was carried out to test the cohesive strength of clots formed when different tested powder compositions were mixed with blood. This parameter was assessed as an indication of the potential hemostatic efficacy of each tested composition. Generally, a higher resistance force (a high value in the Bloom test) correlates with higher cohesive strength and suggests that the composition has a high hemostatic efficacy; low resistance force correlates with low cohesive strength and suggests that the composition has low hemostatic efficacy. The cohesive strength induced by each tested powder composition was evaluated on a comparative basis to the non-supplemented (fine) ORC fibers. The results are presented as fold increase in the resistance force relative to the non-supplemented (fine) ORC fibers.

The modified Bloom test was carried out as follows:
1) 300 mg of each tested powder composition was weighed into a 7 ml tube (interior diameter: 15 mm, height: 50 mm).
2) 2.5 ml of blood (prepared as described above under "Blood preparation") was added to each powder composition.
3) The tube was vortexed vigorously at 3200 rpm until no dry powder was visually apparent and the blood-powder composition mixture was incubated for 3 minutes to enable clot formation.
4) To measure the cohesive strength, the vial was placed in a 'Lloyd LF plus' instrument and a metallic rod [1.27 cm (0.5 inch)] was inserted into the vial at a constant pre-set descending speed: 5 mm/minute. The resistance force of the clot to the movement of the metallic rod at the point of 7 mm extension into the clot was measured in units of megapascal (MPa). The test was carried out at room temperature.

Suture Preclinical Model.

A pulsatile ex-vivo cardiopulmonary bypass (CPB) model was used to simulate physiological conditions. The model is described in:

Sergeant, P., Kocharian, R., Patel, B., Pfefferkorn, M., & Matonick, J. (2016). Needle-to-suture ratio, as well as suture material, impacts needle-hole bleeding in vascular anastomoses. Interactive CardioVascular and Thoracic Surgery, 22(6), 813-816. doi:10.1093/icvts/ivw042.

Briefly, the pulsatile ex-vivo cardiopulmonary bypass model used a series of pumps and chambers to create, control and maintain blood pressure throughout the system. The model consists of a reservoir to filter blood going into and returning from a porcine carotid artery, a computer-integrated data acquisition system, oxygenator and heat exchanger. Flow impedance and volume partitioning adjustments are present to allow for fine adjustment of blood volume flow and pressure control.

The blood loss from the suture placed in the porcine carotid artery was collected and weighed to establish a leak rate. The leak rate was calculated and recorded as the volume of blood collected over a period of time.

To simulate physiological conditions, the following parameters were used:
Pressure of 120/80 mmHg
Pulse rate of 72/min
Blood temperature of 33-35° C.
10,000 IU of heparin were added to 1 L of donor porcine blood and titrated with 10 mg/ml Protamine sulfate to adjust activated clotting time (ACT) to approximately 369 seconds. ACT was measured with a VetScan i-STAT Portable Handheld Unit (Abbott Point of Care) and an I-STAT ACT Celite Cartridge (Abbott Poing of Care, Part#:600-9006-10).

A porcine carotid artery was isolated from the surrounding tissue and mounted on the system. Tubing clamps were used to secure the tissue to the fittings. Blood flow on both sides of the carotid was restricted and the carotid was sutured in a simple continuous pattern with a 6-0 PROLENE Suture (8806H) and a BV-1 needle. Blood loss mass over 2 minutes was measured as a baseline.

The aggregates were applied over the sutured sites and allowed to cure for 4 minutes following complete application. Restriction was removed and the blood loss mass over 2 minutes was measured.

Liver Biopsy Punch In-Vivo Model.

A mature, about 60 kg, female porcine was put on a fast for 24 hours prior to the surgical procedure. The animal was anesthetized with 1150 mg-1400 mg Ketamine, 115 mg-140 mg Xylazine, 7.5 mg Midazolam. Anesthesia was maintained with Isoflurane and the abdomen was opened to reveal the liver. Mean arterial blood pressure, body temperature and heart rate were continuously monitored throughout the surgical procedure. The experiment was terminated when mean arterial blood pressure dropped below 60 mmHg.

A 4 mm diameter×2 mm depth biopsy punch was carried out on the liver lobe and the specimen was excised with surgical scissors. The punch site was allowed to bleed for 30 seconds and bleeding intensity was visually assessed on a scale of 0-5; whereby no bleeding was given a score of 0 and intensive bleeding was given a score of 5. Then, the punch site was wiped with clean gauze to remove excess blood and 100 mg of the tested aggregate composition was poured into the punch cavity (for example, an aggregate composition with 5.0% $CaCl_2$, 2.5% PS and 2.5% εACA is equivalent to: 40 $mg/cm^2$ $CaCl_2$, 20 $mg/cm^2$ PS, 20 $mg/cm^2$ εACA).

A total amount of 100 mg final composition is applied on a circular punch having a diameter of 0.4 cm. Therefore, the 100 mg composition was applied on the punch surface area which is $\pi * (0.2\ cm)^2$ about $0.126\ cm^2$. Meaning that 793.65 $mg/cm^2$ (resulting from the calculation: $100\ mg/0.126\ cm^2$) of final composition was used.

$CaCl_2$ is used at a concentration of 5% of the final composition, therefore 793.65*0.05 equals to about 40 $mg/cm^2$.

PS is used at a concentration of 2.5% of the final composition, therefore 793.65*0.025 equals to about 20 $mg/cm^2$.

εACA is used at a concentration of 2.5% of the final composition, therefore 793.65*0.025 equals to about 20 $mg/cm^2$.

Mild pressure was manually applied over the composition using clean gauze for 1 minute. Bleeding was monitored over a period of 4 minutes, after which bleeding intensity was rated again on a scale of 0-5. The results are presented as percentage of complete hemostasis rate achieved from all replicates.

Example 1: The Effect of Fine ORC Fibers Supplementation with Long ORC Fibers on the Cohesive Strength of a Formed Clot The purpose of this Example was to examine the cohesive strength induced by supplementation of fine ORC fibers with long ORC fibers. The supplementation was carried out by adding increasing amounts of long ORC fibers to fine ORC fibers. The effect was assessed by using a modified Bloom test carried out as described above. Fine ORC fibers were mixed with long ORC fibers (w/w) in the following ratios 100:0, 90:10, 80:20 and 70:30, respectively.

FIG. 1 is a bar graph showing the fold increase of the resistance force/cohesive strength obtained for the different tested compositions as compared to non-supplemented fine ORC fibers.

Results of the modified bloom test demonstrate the force required by the metallic rod to pass through a gel, formed with the tested composition upon contact with blood, at extension of 7 mm whilst moving at a speed of 5 mm/min. This force reflects the level of resistance of the gel (the greater the force, the greater the resistance of the gel) and in turn indicates the level of cohesive strength of a gel. Cohesive strength represents the strength by which molecules of a composition are bound together. The more force required for the rod to proceed with its steady movement, the greater the resistance of the gel and the greater cohesive strength.

The results are presented as fold increase of clot resistance relative to that obtained from non-supplemented fine ORC fibers.

In general, it can be seen that supplementing fine ORC fibers with long ORC fibers increased the clots' resistance and cohesive strength.

The results show that mixture of fine ORC fibers with long ORC fibers increased the cohesive strength of the clot by at least 1.5 times.

Example 2: The Hemostatic Efficacy of Fine ORC Fiber Supplementation with Long ORC Fibers in an Ex-Vivo Model The results obtained in Example 1 showed that supplementing fine ORC fibers with long ORC fibers improved cohesive strength of a clot formed upon mixing the fibers with blood.

In order to examine whether the supplementation that improved cohesive strength can also improve hemostatic capabilities, 3 compositions containing the following amounts of long ORC fibers: 0%, 10% or 25% of the entire composition weight, and all including 5% $CaCl_2$, 2.5% PS, 2.5% εACA were tested in a suture ex-vivo model.

Figure 2:
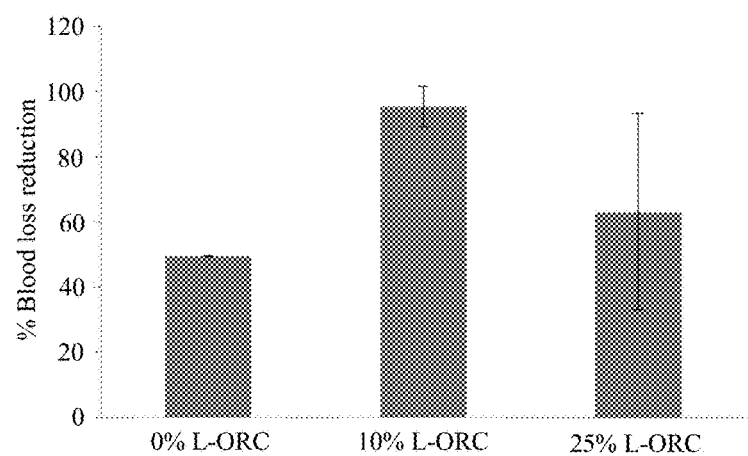
FIG. 2 is a bar diagram showing the hemostatic efficacy for the different aggregates compositions by an ex-vivo suture model. The Figure shows that addition of long ORC fibers (L-ORC) increased the hemostatic efficacy.

The results presented in FIG. 2 demonstrate nearly a two fold increase in the hemostatic efficacy obtained when fine ORC fibers are supplemented with 10% long ORC fibers. When 25% of long ORC are used a positive trend can be observed relative to the non-supplemented fine ORC fibers.

Without being bound by the mechanism, it seems that the long fibers provide a supporting basis for the formed clot which improves the clots' structural integrity, thereby, reducing the chances of blood leaks through the clot and improving the hemostatic efficacy.

Example 3: The Effect Supplementation of Fine Fibers with Long Fibers and Compounds on the Hemostatic Efficacy, Determined by In-Vivo Tests The following example examines the in-vivo hemostatic effect of compounds and fiber supplementation. The results were collected from different pre-clinical experiments carried out on a female porcine using a Liver Biopsy Punch in-vivo model as described above. The results of each experiment are presented in a different table—tables 3, 4 and 5. In this experiment various aggregates compositions were tested. The aggregate compositions tested were ORC fibers with or without supplementation with compounds and long ORC fibers, the concentrations of the compounds and ORC fibers are specified in the Tables below. The supplemented aggregates included ORC fibers combinations of 10.0% (w/w of the final mixture weight) long ORC fibers (see size distribution in table 1A) and 77.5-85.0% fine ORC fibers.

The table lists success rates of complete bleeding arrest/complete hemostasis. In each experiment, fine ORC aggregates (without any supplementation) served as a baseline control to examine the hemostatic efficacy of the supplementation of the compounds and long ORC fibers.

Tables 3, 4 and 5: Complete Hemostasis Rate Obtained after Application of Aggregates Compositions in a Liver Biopsy Punch In-Vivo Model (Number of Replicates in Each Tested Composition≥3).

| Composition Ratio | Complete Hemostasis Rate |
| --- | --- |
| Fine ORC | 25% |
| 2.5:95 PS:ORC<br>2.5:95 εACA:ORC | 0% |
| 5:92.5 CaCl$_2$:ORC<br>2.5:92.5 εACA:ORC | 25% |
| 5:92.5 CaCl$_2$:ORC<br>2.5:92.5 PS:ORC | 0% |
| 5:90 CaCl$_2$:ORC<br>2.5:90 PS:ORC<br>2.5:90 εACA:ORC | 75% |

| Composition Ratio | Complete Hemostasis Rate |
| --- | --- |
| Fine ORC | 0% |
| 3.5:91.5 CaCl$_2$:ORC<br>2.5:91.5 PS:ORC<br>2.5:91.5 εACA:ORC | 0% |
| 6.5:88.5 CaCl$_2$:ORC<br>2.5:88.5 PS:ORC<br>2.5:88.5 εACA:ORC | 37.5% |

| Composition Ratio | Complete Hemostasis Rate |
| --- | --- |
| Fine ORC | 25% |
| 5:91.5 CaCl$_2$:ORC<br>1:91.5 PS:ORC<br>2.5:91.5 εACA:ORC | 20% |
| 5:90 CaCl$_2$:ORC<br>2.5:90 PS:ORC<br>2.5:90 εACA:ORC | 50% |
| 5:87.5 CaCl$_2$:ORC<br>5:87.5 PS:ORC<br>2.5:87.5 εACA:ORC | 40% |
| 5:91.5 CaCl$_2$:ORC<br>2.5:91.5 PS:ORC<br>1:91.5 εACA:ORC | 20% |
| 5:87.5 CaCl$_2$:ORC<br>2.5:87.5 PS:ORC<br>5:87.5 εACA:ORC | 60% |

In this in-vivo model and under the tested conditions (Tables 3-5), superior results by supplementation of fine ORC fibers with long fibers and all three compounds (calcium chloride, PS and εACA) were observed. The positive effect was observed at a specific ratio of the supplements.

The results in Example 2 indicate that there was an improvement in the hemostasis by supplementing with 10% long and including 5% CaCl$_2$, 2.5% PS, and 2.5% εACA.

In this experiment, it is also shown that other ratios had a negative effect and decreased the hemostasis efficacy.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. Hemostatic fibers and/or aggregates composition comprising long and fine cellulose-based fibers comprised of oxidized cellulose and/or oxidized regenerated cellulose, wherein the concentration of the long fibers is in the range of 5%-25% w/w and the concentration of the fine fibers is in the range of 95%-75% w/w of the entire weight composition, wherein the size distribution of the long fibers is: D90 of more than 177 μm and D50 of more than 95 μm, and wherein the size distribution of the fine fibers is: D90 of less than 177 μm, and D50 of less than 95 μm.

2. The hemostatic composition according to claim 1, wherein the D90 of the long fibers is less than 350 μm and the D50 is less than 167 μm.

3. The hemostatic composition according to claim 1, further comprising at least one compound selected from the group consisting of:
   a) a divalent cation selected from zinc, calcium, magnesium, manganese, and copper;
   b) a positively charged peptide and/or polysaccharide;
   c) an omega amino carboxylic acid; and
   d) a combination of any of the above.

4. The hemostatic composition according to claim 1, further comprising protamine salt, calcium salt, and ε-aminocaproic acid (εACA).

5. The hemostatic composition according to claim 1, wherein the cellulose-based fibers are oxidized regenerated cellulose (ORC) fibers.

6. The hemostatic composition according to claim 1, being in the form of aggregates having a size in the range of 75-420 μm.

* * * * *